United States Patent [19]

Bracco et al.

[11] Patent Number: 5,258,179
[45] Date of Patent: Nov. 2, 1993

[54] PROTECTION OF A FOOD, COSMETIC OR PHARMACEUTICAL PRODUCT AGAINST OXIDATION

[75] Inventors: Umberto Bracco, Vevey; Jürg Löliger, Corseaux; Françoise Saucy, Blonay, all of Switzerland

[73] Assignee: Nestec S.A., Vevey, Switzerland

[21] Appl. No.: 10,509

[22] Filed: Jan. 28, 1993

Related U.S. Application Data

[63] Continuation of Ser. No. 589,047, Sep. 27, 1990, abandoned.

[30] Foreign Application Priority Data

Oct. 27, 1989 [CH] Switzerland .......................... 3891/89

[51] Int. Cl.$^5$ .............................................. A61K 31/12
[52] U.S. Cl. .................................... 424/94.1; 514/690; 426/541; 426/544; 426/545; 426/546; 426/321; 426/330.6; 426/330
[58] Field of Search ...................... 424/94.1; 514/690; 426/541, 544, 545, 546, 321, 330.6, 330

[56] References Cited

FOREIGN PATENT DOCUMENTS 55-81813  6/1980  Japan ................................. 514/690
733612   5/1980  U.S.S.R. .......................... 424/544
789063  12/1980  U.S.S.R. .

OTHER PUBLICATIONS

S. Sugiyama, et al. "Anti-Oxidative effect of Coenzyme Q$_{10}$" Experientia 1980, 36(8), 1002-3.
Littaru, et al., "Coenzyme Q and Antioxidant Activity: Facts and Perspectives", *Drugs Exptl. Clin. Res.* X(7) 491-496 (1984).

*Primary Examiner*—Douglas W. Robinson
*Assistant Examiner*—Jean C. Witz
*Attorney, Agent, or Firm*—Vogt & O'Donnell

[57] ABSTRACT

Foods, cosmetics and pharmaceuticals containing a lipid susceptible to oxidation are protected from oxidation by incorporating an effective amount of a coenzyme Q in a lipid phase of the food, cosmetic or pharmaceutical. Ascorbic acid and a phospholipid may be incorporated in combination with the coenzyme Q to provide synergistic protection from oxidation.

18 Claims, No Drawings

PROTECTION OF A FOOD, COSMETIC OR PHARMACEUTICAL PRODUCT AGAINST OXIDATION

CROSS REFERENCE TO RELATED APPLICATION

This is a continuation application of application Ser. No. 07/589,047, filed Sep. 27, 1990, now abandoned.

BACKGROUND OF THE INVENTION

This invention relates to a process for the protection of a fat or a food, cosmetic or pharmaceutical product containing a fat against oxidation and to the use of coenzyme Q as an antioxidant in a food, cosmetic or pharmaceutical product containing a fat.

It is known that the coenzyme Q (CoQ), or ubiquinone, which has been isolated from the lipids of mitochondria, is involved in the basic mechanisms of energy production by respiration, in the transport of electrons in mitochondria and in oxidative phosphorylation. Its antioxidant activity in biological media is known, cf. for example Littarru et al., Fats and Perspectives, Drugs exptl. clin. Res. X (7), 1491–496. However, in a different environment, such as a food, cosmetic or pharmaceutical product containing lipids, the oxidized form, namely quinone, could be expected to have no antioxidant activity because quinones are normally considered to be deactivation products of antioxidants of the hydroquinone type.

SUMMARY OF THE INVENTION

It has now unexpectedly been found that ubiquinone in its quinone form has a significant antioxidant activity in food, cosmetic or pharmaceutical products containing lipids, more particularly in oils rich in polyunsaturated fatty acids.

The process according to the invention is characterized in that an effective quantity of coenzyme Q is incorporated in the fat or in the food, cosmetic or pharmaceutical product.

DETAILED DESCRIPTION OF THE INVENTION

In the context of the invention, the term "food product" is to be understood in a broad sense encompassing products intended for human or animal consumption providing they contain lipids susceptible to oxidation. Similarly, a cosmetic or pharmaceutical product is to be understood in a broad sense intended for topical application or for oral, enteral or parenteral administration providing the product in question contains lipids susceptible to oxidation.

According to the invention, CoQ is understood to be a quinone derivative corresponding to the following formula

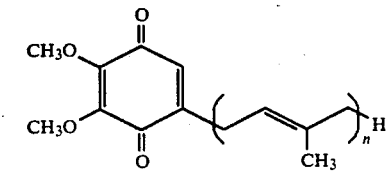

(I)

in which $n=6-10$. The compound $CoQ_{10}$, in which $n=10$, is preferred because it is the most common and, at present, is the only industrially available derivative.

In the process or the use according to the invention, the CoQ is incorporated in the lipid phase of the food, cosmetic or pharmaceutical product in a quantity of 0.1 to 5% by weight, based on the lipids present in the product. If less than 0.1% is added or used, there is a risk that the lipids of the product in question might not be adequately protected. If more than 5% is added or used, the level of protection obtained is not significantly greater than can be obtained by adding quantities in the range indicated.

In one preferred embodiment of the process according to the invention, the CoQ, which is liposoluble, is used in admixture with other antioxidants capable of producing a synergistic effect, for example water-soluble ascorbic acid (AA), in the presence of a natural emulsifier.

In the context of the invention, a "natural emulsifier" is understood to be any of the naturally occurring nonionic surfactants, for example saponins, or ionic surfactants, for example phospholipids, of animal or vegetable origin of milk, egg or soya, preferably lecithins, for example commercial lecithins, purified lecithins, soya lecithin fractions. The nature of the emulsifier used has only a secondary effect on the effect observed providing it is capable of forming a stable dispersion of AA in an anhydrous product, for example a fat or a food containing a fat or a cosmetic or pharmaceutical product containing a fat. It is preferred to use soya lecithins or fractions thereof which are abundant and economical.

The preferred antioxidant mixture suitable for use in accordance with the invention advantageously contains 2.5 to 10% and preferably around 5% of CoQ and 2.5 to 20% and preferably 5 to 20% of AA, based on the weight of natural emulsifier.

It is of course possible to use the mixture as such or to incorporate the various components of the mixture separately from the fat to be protected. In cases where, for example, the fat is a vegetable oil already naturally containining lecithin (LC), for example soybean oil, it is sufficient to add the CoQ and the AA in effective quantities.

In one advantageous embodiment of the preferred variant described above, the mixture is prepared by combining LC and CoQ with stirring at a temperature below or equal to 60° C., preferably while an inert gas, for example nitrogen, is bubbled through. The AA dissolved in a polar solvent, preferably of low boiling point, for example ethanol, is then progressively added to this premix, after which the solvent is eliminated at a temperature of 60° C., for example in a light vacuum. The mixture obtained is in the form of a transparent and viscous liquid. It may be used in different ways, for example by incorporation in a fat to be protected, preferably with heating, the mixture being at approximately 60° C., with vigorous stirring.

In another advantageous embodiment of the preferred variant described above, the AA and the CoQ are incorporated in the fat to which the lecithin has previously been added, preferably in the form of a solution in a polar solvent, for example ethyl alcohol, after which the solvent is eliminated.

The fats to be protected in accordance with the invention are preferably those most sensitive to oxidation, for example fats rich in unsaturated, particularly polyunsaturated, fatty acids, such as vegetable oils, for example wheat germ oil, grape seed oil, corn oil, soybean oil, safflower oil, olive oil, evening primrose oil, borage oil and, in particular, black currant seed oil. Animal fats susceptible to oxidation include chicken fat, butter oil, oils of marine animals, particularly fish oil.

The foods, cosmetic products or pharmaceutical products to be protected are preferably those containing such fats.

The invention is illustrated by the following Examples in which percentages and parts are by weight, unless otherwise indicated.

EXAMPLES

Example 1

Preparation of samples

Samples of 20 g oil stabilized by addition of ubiquinone $CoQ_{10}$ (formula I, n=10) in the quantity indicated are prepared and mixed while stirring, after which the samples are placed in lacquered, sterilized 200 ml tinplate cans in a quantity of 0.5 g stabilized oil per batch per can. The cans are hermetically sealed and stored at 37° C.

Accelerated oxidation test

The head space of the cans containing the samples are analyzed after a certain time (in days) by determining the contents of pentane and ethane as the respective degradation products of linoleic and α-linolenic acid by oxidation and also the residual oxygen content. For comparison, the same analyses are conducted with samples prepared without antioxidant. The pentane and ethane contents are determined by gas-phase chromatography while the oxygen content is determined by measurement of the paramagnetic susceptibility.

The results of this test are set out in Tables 1 and 2 below.

TABLE 1

| Fish oil sample | Storage time (days) | | | | | | | | |
|---|---|---|---|---|---|---|---|---|---|
| | 9 | | | 13 | | | 14 | | |
| | Pentane M | Ethane M | $O_2$ % | Pentane M | Ethane N | $O_2$ % | Pentane M | Ethane M | $O_2$ % |
| With 0.1% $CoQ_{10}$ | $9.55 \cdot 10^{-12}$ | $7.99 \cdot 10^{-11}$ | 14.7 | $9 \cdot 10^{-10}$ | $1.6 \cdot 10^{-8}$ | 0 | — | — | 0 |
| With 1% $CoQ_{10}$ | $2.9 \cdot 10^{-12}$ | $1.88 \cdot 10^{-11}$ | 15.7 | $2.7 \cdot 6^{-10}$ | $3.64 \cdot 10^{-9}$ | 5.9 | $3.39 \cdot 10^{-10}$ | $4.5 \cdot 10^{-10}$ | 4.7 |
| With 5% $CoQ_{10}$ | $2.27 \cdot 10^{-12}$ | $6.45 \cdot 10^{-12}$ | 16.2 | $2.8 \cdot 10^{-11}$ | $2.42 \cdot 10^{-10}$ | 12.7 | $4.99 \cdot 10^{-11}$ | $4.56 \cdot 10^{-10}$ | 11.6 |
| Without $CoQ_{10}$ (comparison) | $1.52 \cdot 10^{-10}$ | $1.54 \cdot 10^{-10}$ | 14.3 | $9 \cdot 10^{-10}$ | $1.61 \cdot 10^{-8}$ | 0 | — | — | 0 |

| Fish oil sample | 15 | | | 16 | | | 17 | | |
|---|---|---|---|---|---|---|---|---|---|
| | Pentane M | Ethane M | $O_2$ | Pentane M | Ethane M. | $O_2$ | Pentane M | Ethane M | $O_2$ |
| With 0.5% $CoQ_{10}$ | — | — | 0 | — | — | 0 | — | — | 0 |
| With 1% $CoQ_{10}$ | $4.22 \cdot 10^{-10}$ | $6.51 \cdot 10^{-10}$ | 4 | $6.62 \cdot 10^{-10}$ | $1.06 \cdot 10^{-8}$ | 1.7 | — | — | 0 |
| With 5% $CoQ_{10}$ | $6.1 \cdot 10^{-11}$ | $5.51 \cdot 10^{-10}$ | 11.5 | $1.17 \cdot 10^{-10}$ | $1.05 \cdot 10^{-9}$ | 9.6 | $1.62 \cdot 10^{-10}$ | $1.83 \cdot 10^{-9}$ | 7.8 |
| Without $CoQ_{10}$ (comparison) | — | — | 0 | 2.3 | — | 0 | — | — | 0 |

| Fish oil sample | 20 | | |
|---|---|---|---|
| | Pentane M | Ethane M | $O_2$ % |
| With 0.1% $CoQ_{10}$ | — | — | 0 |
| With 1% $CoQ_{10}$ | — | — | 0 |
| With 5% $CoQ_{10}$ | $3.76 \cdot 10^{-10}$ | $5.96 \cdot 10^{-9}$ | 0.6 |
| Without $CoQ_{10}$ (comparison) | — | — | 0 |

Legend:
—: not determined, excessively high value

TABLE 2

| black currant seed oil sample | Storage time (days) | | | | | |
|---|---|---|---|---|---|---|
| | 25 | | | 27 | | |
| | Pentane M | Ethane M | $O_2$ % | Pentane M | Ethane M | $O_2$ % |
| With 0.1% $CoQ_{10}$ | $5.44 \cdot 10^{-11}$ | $3.51 \cdot 6^{-11}$ | 13.6 | $4.09 \cdot 10^{-11}$ | $2.9 \cdot 10^{-11}$ | 13.6 |
| With 1% $CoQ_{10}$ | $1.4 \cdot 10^{-11}$ | $9.42 \cdot 10^{-12}$ | 14.4 | $4.6 \cdot 10^{-10}$ | $2.61 \cdot 10^{-10}$ | 11.2 |
| With 5% $CoQ_{10}$ | x | x | x | $6.55 \cdot 10^{-11}$ | $4.17 \cdot 10^{-11}$ | 13.1 |
| Without $CoQ_{10}$ (comparison) | $2.71 \cdot 10^{-10}$ | $1.64 \cdot 10^{-10}$ | 12.1 | $1.01 \cdot 10^{-8}$ | $4.35 \cdot 10^{-9}$ | 4.6 |

| black currant seed oil sample | 28 | | | 30 | | | 31 | | |
|---|---|---|---|---|---|---|---|---|---|
| | Pentane M | Ethane M | $O_2$ | Pentane M | Ethane M | $O_2$ | Pentane M | Ethane M | $O_2$ |
| With 0.5% $CoQ_{10}$ | $4.76 \cdot 10^{-9}$ | $2.2 \cdot 10^{-9}$ | 5.9 | — | — | 0 | — | — | 0 |
| With 1% $CoQ_{10}$ | $1.9 \cdot 10^{-10}$ | $1.14 \cdot 10^{-10}$ | 12.6 | $3.68 \cdot 10^{-9}$ | $1.65 \cdot 10^{-9}$ | 7.1 | $3.11 \cdot 10^{-8}$ | $1.15 \cdot 10^{-8}$ | 0 |
| With 5% $CoQ_{10}$ | $3.38 \cdot 10^{-10}$ | $1.76 \cdot 10^{-10}$ | 11.7 | $8.44 \cdot 10^{-11}$ | $4.97 \cdot 10^{-11}$ | 12.8 | $8.38 \cdot 10^{-10}$ | $4.12 \cdot 10^{-10}$ | 9 |
| Without $CoQ_{10}$ | $1.31 \cdot 10^{-8}$ | $5.47 \cdot 10^{-9}$ | 2.9 | — | — | 0 | — | — | 0 |

| black currant seed oil sample | 34 | | |
|---|---|---|---|
| | Pentane M | Ethane M | $O_2$ %. |
| With 0.1% $CoQ_{10}$ | — | — | 0 |
| With 1% $CoQ_{10}$ | — | — | 0 |

TABLE 2-continued

|  | | | |
|---|---|---|---|
| With 5% $CoQ_{10}$ | $5.58 \cdot 10^{-9}$ | $2.15 \cdot 10^{-9}$ | 4.4 |
| Without $CoQ_{10}$ (comparison) | — | — | 0 |

Legend:
—: not determined, excessively high value
x: not measured

The above results clearly demonstrate the antioxidant activity of $CoQ_{10}$ in fish oil and black currant seed oil by comparison with the same oils without $CoQ_{10}$.

Example 2

The procedure described in Example 1 is again used to measure the pentane, ethane and oxygen contents of the head space of 200 ml cans containing 0.5 g fish oil stabilized with 2.1 0.1% $CoQ_{10}$
2.2 0.1% $CoQ_{10}$ and 1% purified soya lecithin (Topcithin ®, LC)
2.3 0.1% $CoQ_{10}$, 1% Topcithin ® and 1,000 ppm (parts per million) ascorbic acid (AA)

and stored at 37° C. for the period indicated (days).

The pentane, ethane and oxygen contents of the head space of the cans containing the fish oil without stabilizer ($C_1$), with 1,000 ppm AA ($C_2$) and finally with 1,000 ppm AA+1% LC ($C_3$) are determined for comparison.

The results obtained are shown in Table 3 below.

TABLE 3

| Fish oil Sample | Storage time (days) | | | | | | | | |
|---|---|---|---|---|---|---|---|---|---|
| | 12 | | | 19 | | | 41 | | |
| | Pentane M | Ethane M | $O_2$ % | Pentane M | Ethane M | $O_2$ % | Pentane M | Ethane M | $O_2$ % |
| 2.1 | $1.38 \cdot 10^{-11}$ | $9.77 \cdot 10^{-11}$ | 13.3 | $4.96 \cdot 10^{-10}$ | $6.76 \cdot 10^{-9}$ | 2 | — | — | 0 |
| 2.2 | $1.21 \cdot 10^{-12}$ | $1.04 \cdot 10^{-11}$ | 14.6 | $2.01 \cdot 10^{-11}$ | $2.55 \cdot 10^{-10}$ | 12.2 | — | — | 0 |
| 2.3 | $5.53 \cdot 10^{-12}$ | $3.59 \cdot 10^{-12}$ | 15.4 | $8 \cdot 10^{-12}$ | $8 \cdot 10^{-12}$ | 15.4 | $1.73 \cdot 10^{-10}$ | $3.14 \cdot 10^{-9}$ | 8 |
| $C_1$ | $2.02 \cdot 10^{-11}$ | $1.21 \cdot 10^{-10}$ | 13.1 | $8.56 \cdot 10^{-10}$ | $1.38 \cdot 10^{-8}$ | 0 | — | — | 0 |
| $C_2$ | $2 \cdot 10^{-11}$ | $1.01 \cdot 10^{-11}$ | 13 | $8 \cdot 10^{-10}$ | $0.67 \cdot 10^{-8}$ | 0.5 | — | — | 0 |
| $C_3$ | $1.8 \cdot 10^{-11}$ | $0.9 \cdot 10^{-10}$ | 12.9 | $7.8 \cdot 10^{-10}$ | $0.9 \cdot 10^{-8}$ | 0.6 | — | — | 0 |

Legend: —: not determined, excessively high value

The above results clearly show that the combination of $CoQ_{10}$, AA and LC in the quantities used affords fish oil effective protection against oxidation, even after storage for 41 days, whereas without stabilizer ($C_1$) fish oil oxidizes rapidly from the 12th day. In addition, the use of AA alone ($C_2$) or in admixture with LC ($C_3$) no longer affords fish oil protection against oxidation from the 19th day.

We claim:

1. A process for protecting a lipid-containing cosmetic from oxidation consisting essentially of incorporating in the lipid phase of the cosmetic a coenzyme Q, a phospholipid, and ascorbic acid to protect the cosmetic from oxidation, wherein the coenzyme Q is incorporated in the cosmetic in an amount of from 0.1% to 5% by weight based upon a weight of the lipid in the cosmetic and wherein the ascorbic acid is incorporated in the cosmetic in an amount of from 2.5% to 20% by weight, based upon the weight of the phospholipid.

2. A process according to claim 1 wherein from 2.5% to 10% by weight coenzyme Q is incorporated in the cosmetic, based on a weight of the phospholipid.

3. A process according to claim 1 wherein the coenzyme Q is coenzyme $Q_{10}$.

4. A process according to claim 1 wherein the phospholipid is a lecithin.

5. A process according to claim 1 wherein the cosmetic contains black currant seed oil.

6. A process according to claim 1 wherein the cosmetic contains fish oil.

7. A process for protecting a lipid-containing pharmaceutical from oxidation consisting essentially of incorporating in the lipid phase of the pharmaceutical a coenzyme Q, a phospholipid and ascorbic acid to protect the pharmaceutical from oxidation, wherein the coenzyme Q is incorporated in the pharmaceutical in an amount of from 0.1% to 5% by weight based upon a weight of the lipid in the pharmaceutical and wherein the ascorbic acid is incorporated in the pharmaceutical an am amount of from 2.5% to 20% by weight, based upon the weight of the phospholipid.

8. A process according to claim 7 wherein from 2.5% to 10% by weight coenzyme Q is incorporated in the pharmaceutical, based on a weight of the phospholipid.

9. A process according to claim 7 wherein the coenzyme Q is coenzyme $Q_{10}$.

10. A process according to claim 7 wherein the phospholipid is a lecithin.

11. A process according to claim 7 wherein the pharmaceutical contains black currant seed oil.

12. A process according to claim 7 wherein the pharmaceutical composition contains fish oil.

13. A process for protecting a lipid-containing food from oxidation consisting essentially of incorporating in the lipid phase of the food a coenzyme Q, a phospholipid and ascorbic acid to protect the pharmaceutical from oxidation, wherein the coenzyme Q is incorporated in the food in an amount of from 0.1% to 5% by weight based upon a weight of the lipid in the food and wherein the ascorbic acid is incorporated in the food in an amount of from 2.5% to 20% by weight, based upon the wieght of the phospholipid.

14. A process according to claim 13 wherein from 2.5% to 10% by weight coenzyme Q is incorporated in the food, based on a weight of the phospholipid.

15. A process according to claim 13 wherein the coenzyme Q is coenzyme $Q_{10}$.

16. A process according to claim 13 wherein the phospholipid is a lecithin.

17. A process according to claim 13 wherein the food contains black currant seed oil.

18. A process according to claim 13 wherein the food contains fish oil.

* * * * *

UNITED STATES PATENT AND TRADEMARK OFFICE
CERTIFICATE OF CORRECTION

PATENT NO. : 5,258,179
DATED : November 2, 1993
INVENTOR(S) : Umberto BRACCO, et al.

It is certified that error appears in the above-identified patent and that said Letters Patent is hereby corrected as shown below:

Column 6, line 21 (line 9 of claim 7), "an am" should be --in an--.

Column 6, line 56 (line 10 of claim 13), "wieght" should be --weight--.

Signed and Sealed this

Ninth Day of May, 1995

BRUCE LEHMAN

Attest:

Attesting Officer

Commissioner of Patents and Trademarks